US008870983B2

(12) United States Patent
Baustian et al.

(10) Patent No.: US 8,870,983 B2
(45) Date of Patent: Oct. 28, 2014

(54) OXYGENATED BUTANOL GASOLINE COMPOSITION HAVING GOOD DRIVEABILITY PERFORMANCE

(75) Inventors: James J. Baustian, St. Charles, IL (US); Leslie R. Wolf, Naperville, IL (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 218 days.

(21) Appl. No.: 13/162,184

(22) Filed: Jun. 16, 2011

(65) Prior Publication Data

US 2012/0151996 A1    Jun. 21, 2012

Related U.S. Application Data

(60) Provisional application No. 61/355,224, filed on Jun. 16, 2010.

(51) Int. Cl.
*C10L 1/18* (2006.01)
*C10L 1/02* (2006.01)
*C10L 1/06* (2006.01)

(52) U.S. Cl.
CPC .. *C10L 1/023* (2013.01); *C10L 1/06* (2013.01)
USPC ............................................. 44/451; 44/452

(58) Field of Classification Search
USPC .................................................. 44/451, 452
See application file for complete search history.

(56) References Cited

U.S. PATENT DOCUMENTS

| 1,774,180 | A | * | 8/1930 | Mann, Jr. ...................... 44/452 |
| 5,755,833 | A | | 5/1998 | Ishida et al. |
| 5,782,937 | A | | 7/1998 | Colucci et al. |
| 6,083,288 | A | | 7/2000 | Wolf |
| 2008/0261230 | A1 | | 10/2008 | Liao et al. |
| 2009/0277079 | A1 | * | 11/2009 | Baustian ........................ 44/451 |

FOREIGN PATENT DOCUMENTS

| WO | 2006081089 | 8/2006 |
| WO | 2009102608 | 8/2009 |
| WO | 2009137356 | 11/2009 |

OTHER PUBLICATIONS

International Search Report and Written Opinion of corresponding PCT/US2011/040707 mailed Sep. 30, 2011.

* cited by examiner

*Primary Examiner* — Cephia D Toomer

(57) ABSTRACT

A gasoline blend and a method for producing a gasoline blend containing low concentrations of a butanol isomer and having good cold start and warm-up driveability characteristics are disclosed.

22 Claims, 5 Drawing Sheets

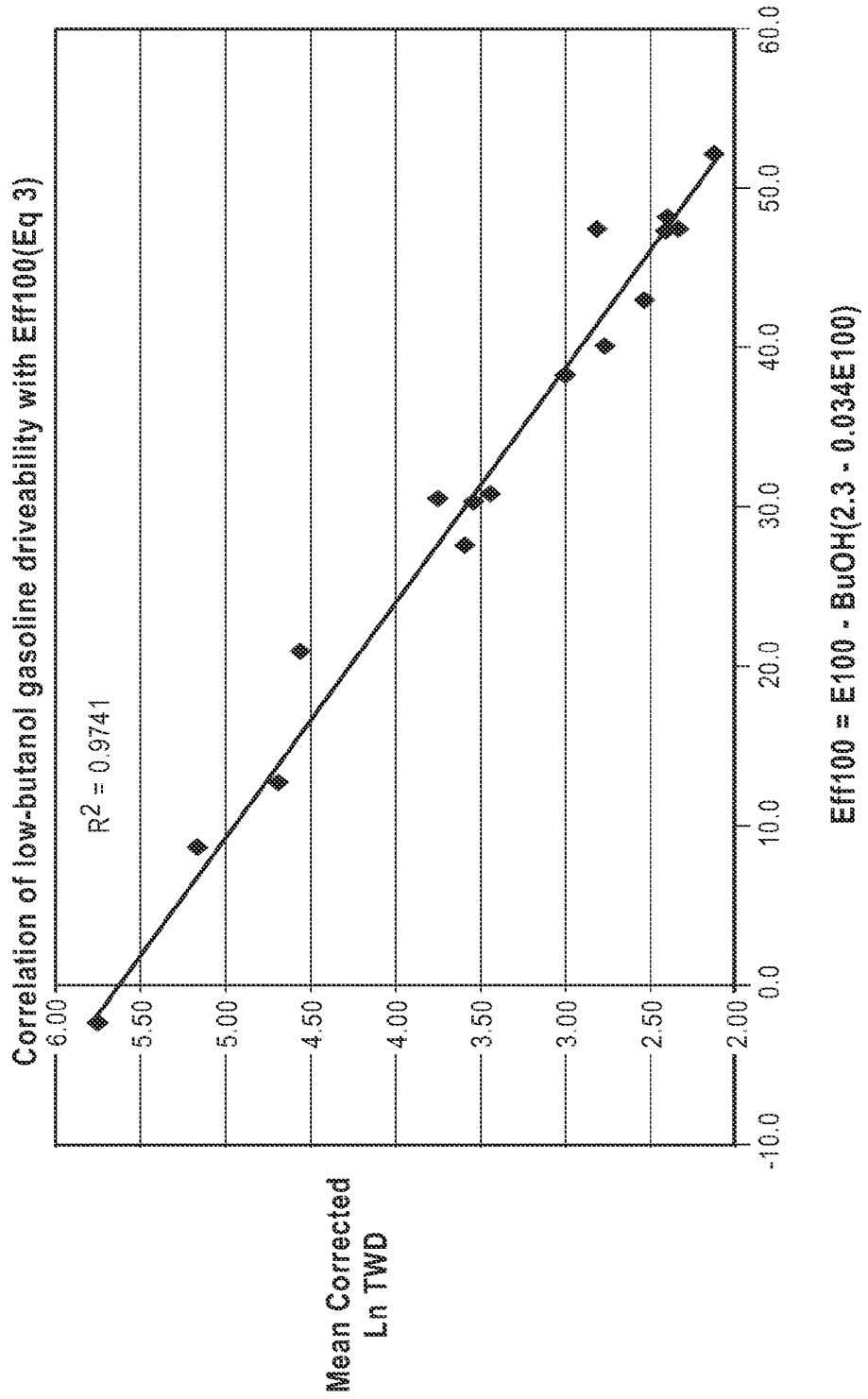

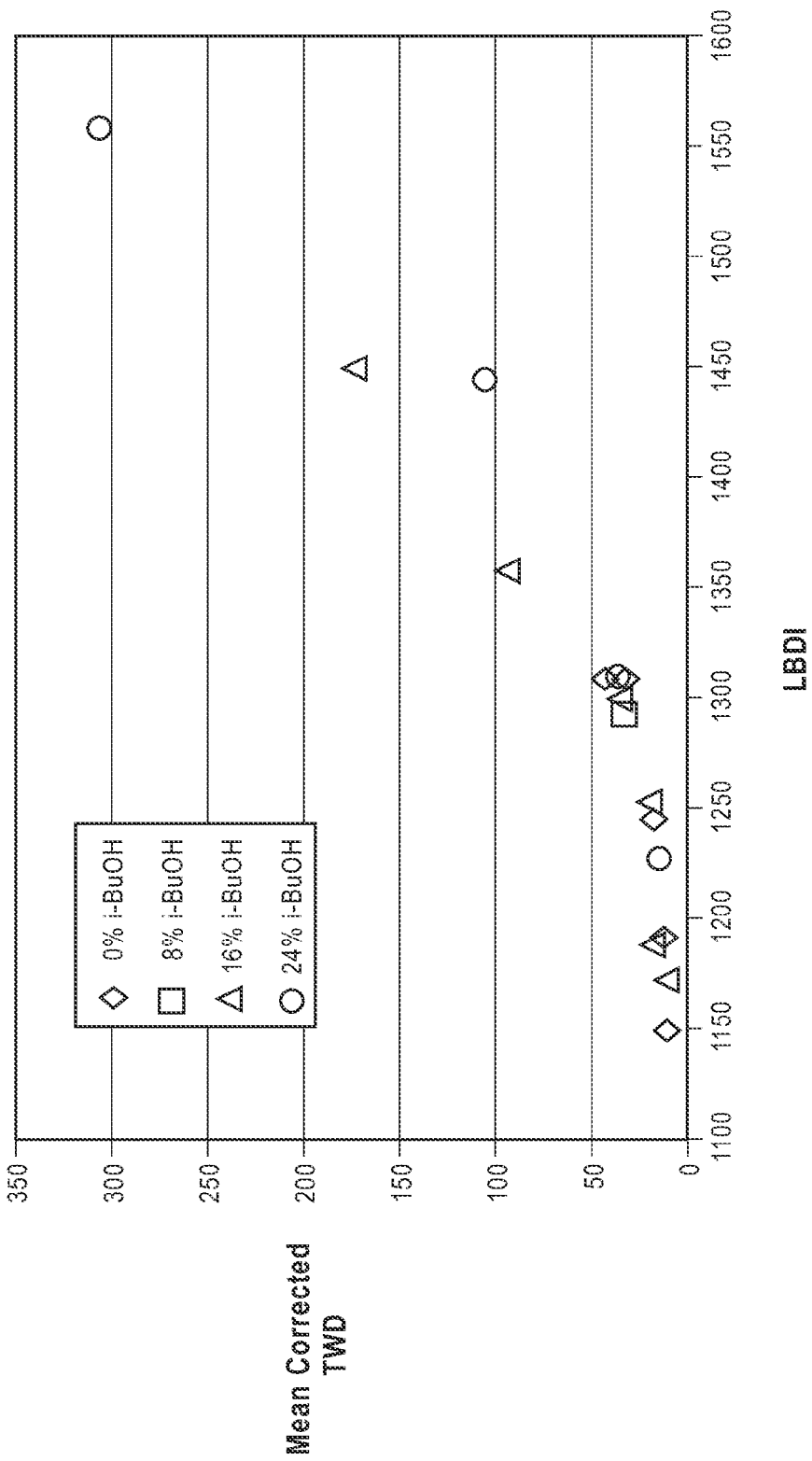

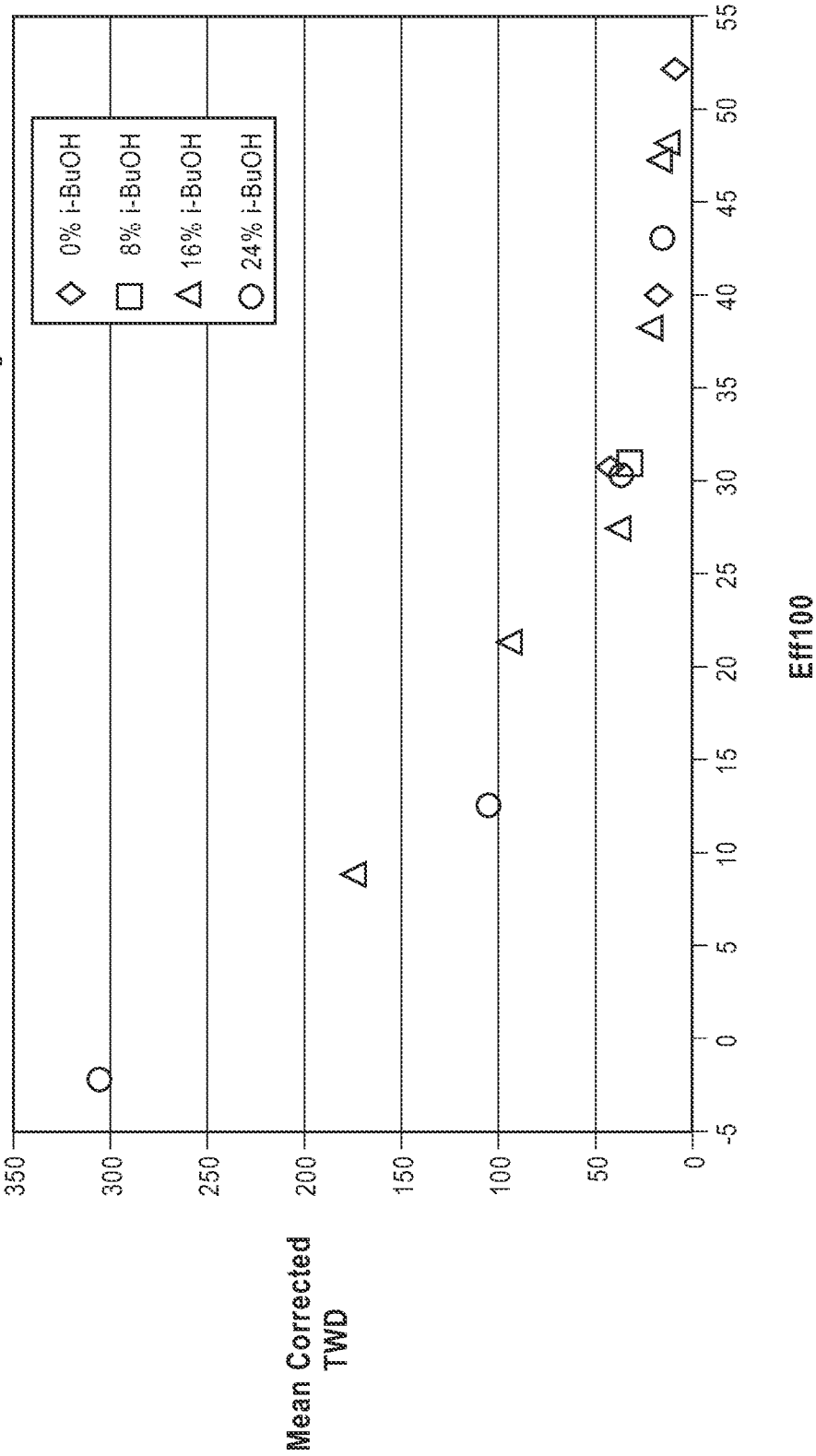

US 8,870,983 B2

OXYGENATED BUTANOL GASOLINE COMPOSITION HAVING GOOD DRIVEABILITY PERFORMANCE

CROSS-REFERENCE TO RELATED APPLICATIONS

The present application claims the benefit of U.S. Provisional Patent Application No. 61/355,224, filed Jun. 16, 2010, the contents of which are fully incorporated herein by reference.

BACKGROUND OF THE INVENTION

This invention relates to fuels, more particularly to oxygenated gasolines including gasolines containing butanol and optionally ethanol. This invention provides an oxygenated butanol gasoline having good cold start and warm-up driveability performance.

Gasolines are fuels which are suitable for use in a spark-ignition engine and which generally contain as a primary component a mixture of numerous hydrocarbons having different boiling points and typically boiling at a temperature in the range of from about 79° F. to about 437° F. under atmospheric pressure. This range is approximate and can vary depending upon the actual mixture of hydrocarbon molecules present, the additives or other compounds present (if any), and the environmental conditions. Typically, the hydrocarbon component of gasolines contains $C_4$ to $C_{10}$ hydrocarbons.

Gasolines are typically required to meet certain physical and performance standards. Some characteristics may be implemented for proper operation of engines or other fuel combustion apparatuses. However, many physical and performance characteristics are set by national or regional regulations for other reasons such as environmental management. Examples of physical characteristics can include Reid Vapor Pressure, sulfur content, oxygen content, aromatic hydrocarbon content, benzene content, olefin content, the temperature at which 90 percent of the fuel is distilled (T90), the temperature at which 50 percent of the fuel is distilled (T50) and others. Performance characteristics can include octane rating, combustion properties, and emission components.

For example, standards for gasolines for sale within much of the United States are generally set forth in ASTM Standard Specification Number D 4814 ("ASTM D 4814") which is incorporated herein by reference. Additional federal and state regulations may supplement this ASTM standard. Standards for gasolines for sale within much of Europe are generally set forth in European Standard EN228:2008, which is also incorporated herein by reference.

The specifications for gasolines set forth in ASTM D 4814 vary based on a number of parameters affecting volatility and combustion such as weather, season, geographic location and altitude. For this reason, gasolines produced in accordance with ASTM D 4814 are broken into vapor pressure/distillation AA, A, B, C, D and E, and vapor lock protection classes 1, 2, 3, 4, 5, and 6, each category having a set of specifications describing gasolines meeting the requirements of the respective classes. These specifications also set forth test methods for determining the parameters in the specification.

For example, a Class AA-2 gasoline blended for use during the summer driving season in relatively warm climates must have a maximum vapor pressure of 7.8 psi, a maximum temperature for distillation of 10 percent of the volume of its components (the "T10") of 158° F., a temperature range for distillation of 50 percent of the volume of its components (the "T50") of between 170° F. and 250° F., a maximum temperature for distillation of 90 percent of the volume of its components (the "T90") of 374° F., a distillation end point of 437° F., a distillation residue maximum of 2 volume percent, and a maximum "Driveability Index" or "DI", as described below, of 1250.

Cold start and warm-up (CS&W) performance is a key quality indicator for gasoline motor fuels; properly formulated gasoline fuels enable a cold engine (i.e., an engine which is essentially the same temperature as its surroundings with no residual heat from previous running) to start quickly and provide smooth drive-away performance under all climatic conditions. The startup and driveaway performance should be free from faults such as long cranking time, stalls, and stumble or hesitation on acceleration.

The CS&W performance of gasoline is controlled by the fuel's volatility properties traditionally including the vapor pressure and especially the distillation properties (that is, the distribution of component boiling temperatures across the fuel's boiling range). Product specifications in the US (ASTM), Europe (EN), and other regions employ limits on these individual properties, as well as limits on property combinations (for example, the ASTM Driveability Index originally consisted of a linear combination of three distillation temperatures), which have been indexed against observed CS&W driveability performance across the preponderance of vehicles and conditions in which the fuels are employed.

The introduction of bio-components to the gasoline blending pool (most notably ethanol at 10 vol % in the US) precipitated a revision of gasoline volatility specifications to ensure acceptable CS&W driveability. Specifically the ASTM Driveability Index employed in the United States was modified to include a term for ethanol content as:

$$\text{ASTM Driveability Index(DI)}=1.5T_{10}+3T_{50}+T_{90}+2.4\text{EtOH} \quad \text{(Eq. 1)}$$

where $T_{10}$, $T_{50}$, and $T_{90}$ are the observed temperatures in ° F. for the distillation of 10, 50 and 90 volume percent of the fuel in a standard ASTM D86 distillation test and EtOH is the fuel's ethanol concentration in volume percent. Inclusion of the ethanol term was found to produce an improved index for the observed performance of vehicles in controlled CS&W driveability tests. The specifications establish a maximum value of DI for each vapor pressure/distillation class in Table 1 of D4814 and, hence, for each seasonal volatility class in D4814 Table 4; fuels with DI above the specification maximum are expected to have degraded CS&W performance.

In European applications, the EN228 gasoline specification controls mid-range volatility for good CS&W driveability by specifying a minimum volume percent E100 of the fuel that must be distilled by 100° C. in the standard distillation test.

However, controlled experiments indicated that CS&W driveability performances can be problematic for gasoline blends that contain a high concentration of a butanol isomer. It was also found that existing methods for predicting CS&W driveability performance from fuel volatility parameters, such as the aforesaid Driveability Index (Eq. 1) are ineffective for high-butanol blends. Baustian, U.S. patent application Ser. No. 12/431,217, filed Apr. 28, 2009, discloses a method for producing a gasoline blend having a high concentration of at least one butanol isomer which comprises maintaining at least 35 volume percent the volume fraction of the blend that distills at temperatures up to about 200° F.

Because butanol isomers boil near the midpoint of gasoline, it is generally understood that butanol could be blended at relatively low concentrations with gasoline without significantly altering the evaporation characteristics of the fuel.

However, blending isobutanol under various conditions in a way that improves cold start and warm-up (CS&W) driveability, while maximizing renewable fuel component blending, is not understood. Therefore, it is highly desirable to develop a modified driveability index and method that affords the production of gasoline blends that can also contain lower levels of at least one biologically-sourced butanol isomer, and in particular, isobutanol, to maximize both the CS&W driveability and the renewable components of a butanol gasoline blend.

SUMMARY OF THE INVENTION

In one aspect, the present invention is a method for producing a butanol gasoline blend having good cold start and warm-up (CS&W) driveability performance comprising: (a) blending at least one biologically-sourced butanol isomer and optionally ethanol with gasoline to form a butanol gasoline blend, the butanol gasoline blend having a vapor pressure corresponding to a specific ASTM D4814 vapor pressure/distillation class of gasoline; wherein the butanol gasoline blend has a value of low butanol driveability index (LBDI) equal to the linear combination $a_1T_{10}+a_2T_{50}+a_3T_{90}+a_4EtOH+BuOH(a_5-a_6E200)$ below the maximum limit for Driveability Index (DI) for the specific class of gasoline; wherein: $T_{10}$ is the temperature for distillation of 10-volume percent of the butanol gasoline blend; $T_{50}$ is the temperature for distillation of 50-volume percent of the butanol gasoline blend; $T_{90}$ is the temperature for distillation of 90-volume percent of the butanol gasoline blend; EtOH is the concentration in volume percent of ethanol in the butanol gasoline blend; BuOH is the concentration in volume percent of the at least one biologically-sourced butanol isomer in the butanol gasoline blend; E200 is the volume percent of the butanol gasoline blend that distills at temperatures up to about 200° F.; the maximum limit for the Driveability Index (DI) for the specific class of gasoline is specified in Table 1 of ASTM D 4814-08a; and $a_1, a_2, a_3, a_4, a_5$ and $a_6$ are coefficients selected to give a substantially linear relationship between the values of the linear combination for the butanol gasoline blend containing the at least one butanol isomer and optionally ethanol and the logarithms of the mean corrected total weighted demerits from test measurements of CS&W driveability performance for such blends, at concentrations of ethanol less than about 20 volume percent, at concentrations of the at least one biologically-sourced butanol isomer less than about 30 volume percent, and at total concentrations of ethanol and the at least one biologically-sourced butanol isomer less than about 35 volume percent; and wherein the total weighted demerits of the butanol gasoline blend is less than about 40.

In another aspect, the present invention is a butanol gasoline blend having good cold start and warm-up (CS&W) driveability performance comprising: a specific ASTM D4814 vapor pressure/distillation class of gasoline; at least one biologically-sourced butanol isomer and optionally ethanol; the butanol gasoline blend having a vapor pressure corresponding to a specific ASTM D4814 Table 1 vapor pressure/distillation class of gasoline; wherein the butanol gasoline blend has a value of low butanol driveability index (LBDI) equal to the linear combination $a_1T_{10}+a_2T_{50}+a_3T_{90}+a_4EtOH+BuOH(a_5-a_6E200)$ below the specified maximum limit for Driveability Index (DI) for the specific class of gasoline; wherein $T_{10}$ is the temperature for distillation of 10-volume percent of the butanol gasoline blend; $T_{50}$ is the temperature for distillation of 50-volume percent of the butanol gasoline blend; $T_{90}$ is the temperature for distillation of 90-volume percent of the butanol gasoline blend; EtOH is the concentration in volume percent of ethanol in the butanol gasoline blend; BuOH is the concentration in volume percent of the at least one biologically-sourced butanol isomer in the butanol gasoline blend; E200 is the volume percent of the butanol gasoline blend that distills at temperatures up to about 200° F.; the maximum limit for the Driveability Index (DI) for the specific class of gasoline is specified in Table 1 of ASTM D 4814; and $a_1, a_2, a_3, a_4, a_5$ and $a_6$ are coefficients selected to give a substantially linear relationship between the values of the linear combination for the butanol gasoline blend containing the at least one butanol isomer and optionally ethanol and the logarithms of the mean corrected measured total weighted demerits from test measurements of CS&W driveability performance for such blends, at concentrations of ethanol less than about 20 volume percent, at concentrations of the at least one biologically-sourced butanol isomer less than about 30 volume percent, and at total concentrations of ethanol and the at least one biologically-sourced butanol isomer less than about 35 volume percent; and wherein the total weighted demerits of the butanol gasoline blend is less than about 40.

In another aspect, the present invention is a method for producing a butanol gasoline blend having good cold start and warm-up (CS&W) driveability performance comprising: (a) blending at least one biologically-sourced butanol isomer and optionally ethanol with gasoline, to form a butanol gasoline blend, the butanol gasoline blend having a vapor pressure corresponding to a specific EN228 volatility class of gasoline; wherein the butanol gasoline blend has an $Eff_{100}$ value equal to the linear combination $E100-BuOH(b_1-b_2E 100)$ above the minimum limit for E100 for that class of gasoline as specified in Table 2 of EN228; wherein BuOH is the concentration in volume percent of the at least one biologically-sourced butanol isomer in the butanol gasoline blend; E100 is the volume percent of the butanol gasoline blend that distills at temperatures up to about 100° C.; and $b_1$ and $b_2$ are coefficients selected to give a substantially linear relationship between the values of the linear combination for the butanol gasoline blends containing the at least one butanol isomer and optionally ethanol and the logarithms of the mean corrected measured total weighted demerits for such blends, at concentrations of ethanol less than about 20 volume percent, at concentrations of the at least one biologically-sourced butanol isomer less than about 30 volume percent, and at total concentrations of ethanol and the at least one biologically-sourced butanol isomer less than about 35 volume percent, and wherein the total weighted demerits of the butanol gasoline blend is less than about 40.

In another aspect, the present invention is a butanol gasoline blend having good cold start and warm-up (CS&W) driveability performance comprising: a blend of a specific EN228 volatility class of gasoline, at least one biologically-sourced butanol isomer, and optionally ethanol, the butanol gasoline blend having a vapor pressure corresponding to a specific EN228 Table 2 volatility class of gasoline; wherein the butanol gasoline blend has an $Eff_{100}$ value equal to the linear combination $E100-BuOH(b_1-b_2E100)$, and is above the minimum limit for E100 as specified in Table 2 of EN228; wherein BuOH is the at least one biologically-sourced butanol isomer concentration in volume percent in the butanol gasoline blend; E100 is the volume percent of the butanol gasoline blend that distills at temperatures up to about 100° C.; and $b_1$ and $b_2$ are coefficients selected to give a substantially linear relationship between the values of the linear combination for the butanol gasoline blends containing the at least one butanol isomer and optionally ethanol and the logarithms of the mean corrected measured total weighted demerits for such blends, at concentrations of ethanol less than about 20 volume percent, at concentrations of the at least one biologically-sourced butanol isomer less than about 30 volume percent, and at total concentrations of ethanol and the at least one biologically-sourced butanol isomer less than about 35 volume percent; and wherein the total weighted demerits of the butanol gasoline blend is less than about 40.

In another aspect, the invention is a method of identifying a butanol gasoline blend having good cold start and warm-up (CS&W) driveability performance comprising: (a) blending gasoline with butanol, and optionally, ethanol; (b) measuring fuel variables E200, $T_{10}$, $T_{50}$, and $T_{90}$; (c) inputting the fuel variables in an equation $a_1 T_{10} + a_2 T_{50} + a_3 T_{90} + a_4 EtOH + BuOH$ ($a_5 - a_6 E200$) to calculate a LBDI of the butanol gasoline blend; and (d) comparing the LBDI to a maximum limit for driveability index (DI) for the specific class of gasoline; wherein the butanol gasoline blend has good cold start and warm-up (CS&W) driveability performance if the LBDI is below the maximum limit for the Driveability Index (DI) for the class of gasoline specified in Table 1 of ASTM D 4814; wherein $T_{10}$ is the temperature for distillation of 10-volume percent of the butanol gasoline blend; $T_{50}$ is the temperature for distillation of 50-volume percent of the butanol gasoline blend; $T_{90}$ is the temperature for distillation of 90-volume percent of the butanol gasoline blend; EtOH is the concentration in volume percent of ethanol in the butanol gasoline blend; BuOH is the concentration in volume percent of the at least one biologically-sourced butanol isomer in the butanol gasoline blend; E200 is the volume percent of the butanol gasoline blend that distills at temperatures up to about 200° F.; $a_1$, $a_2$, $a_3$, $a_4$, $a_5$ and $a_6$ are coefficients selected to give a substantially linear relationship between the values of the linear combination for the butanol gasoline blends containing the at least one butanol isomer and optionally ethanol and the logarithms of the mean corrected measured total weighted demerits for such blends, at concentrations of ethanol less than about 20 volume percent, at concentrations of the at least one biologically-sourced butanol isomer less than about 30 volume percent, and at total concentrations of ethanol and the at least one biologically-sourced butanol isomer less than about 35 volume percent.

BRIEF DESCRIPTION OF THE DRAWINGS

FIG. 3 is a plot of the mean corrected natural logarithm of total weighted demerits of low butanol gasoline driveability versus $Eff_{100}$.

FIG. 4 is a re-plot of the data plotted in FIG. 2, except that the mean corrected total weighted demerits rather than their log transforms are plotted on the y-axis.

FIG. 5 is a re-plot of the data plotted in FIG. 3, except that the mean corrected total weighted demerits rather than their log transforms are plotted on the y-axis.

DETAILED DESCRIPTION OF THE INVENTION

Figure 1:
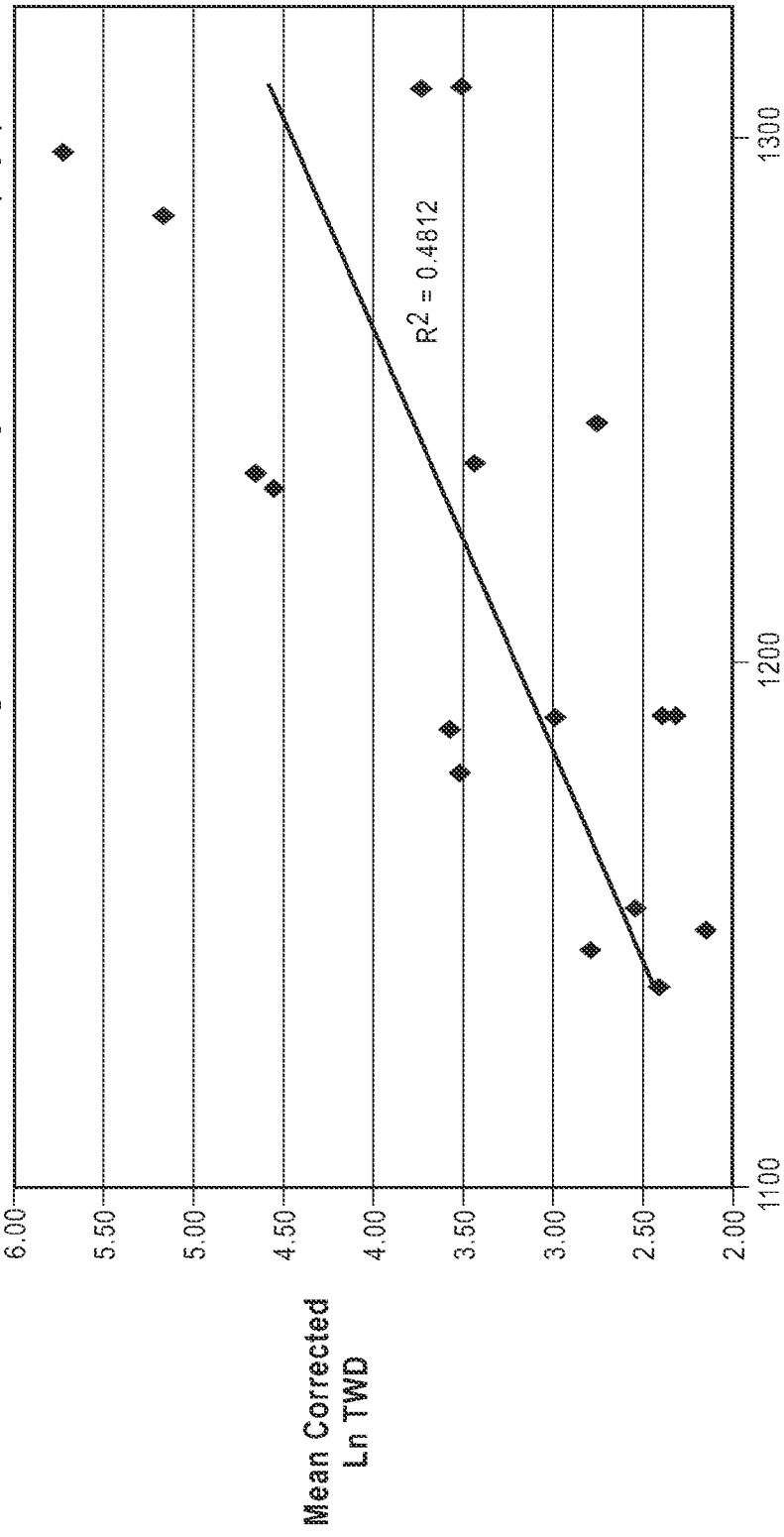
FIG. 1 is a plot of the mean corrected natural logarithm of total weighted demerits of low butanol gasoline driveability versus ASTM DI.

Unless defined otherwise, all technical and scientific terms used herein have the same meaning as commonly understood by one of ordinary skill in the art to which this invention belongs. In the case of a conflict, the present application including the definitions will control. Also, unless otherwise required by context, singular terms shall include pluralities and plural terms shall include the singular. All publications, patents and other references mentioned herein are incorporated by reference in their entireties for all purposes.

In order to further define this invention, the following terms and definitions are herein provided.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers may be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The terms "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value; in another embodiment, within 5% of the reported numerical value.

The term "substantial" and "substantially" as used herein, means a deviation of up to 10%, preferably up to 5% is allowed.

The term "alcohol" as used herein refers to any of a series of hydroxyl compounds, the simplest of which are derived from saturated hydrocarbons, having the general formula $C_nH_{2n+1}OH$. Examples of alcohol include ethanol and butanol.

The term "butanol" as used herein, refers to n-butanol, 2-butanol, isobutanol, tert-butyl alcohol, individually or any mixtures thereof. The butanol can be biologically-sourced (i.e., biobutanol), for example. Biologically-sourced refers to fermentative production. See, e.g., U.S. Pat. No. 7,851,188, herein incorporated by reference in its entirety.

The terms "renewable component" as used herein, refers to a component that is not derived from petroleum or petroleum products.

The term "fuel" as used herein, refers to any material that can be used to generate energy to produce mechanical work in a controlled manner. Examples of fuels include, but are not limited to, biofuels (i.e., fuels which are in some way derived from biomass), gasoline, gasoline subgrades, diesel and jet fuel. It is understood that the specific components and allowances of suitable fuels can vary based on seasonal and regional guidelines.

The terms "fuel blend" or "blended fuel" as used herein, refer to a mixture containing at least a fuel and one or more alcohols.

The term "gasoline" as used herein, generally refers to a volatile mixture of liquid hydrocarbons that can optionally contain small amounts of additives. This term includes, but is not limited to, conventional gasoline, oxygenated gasoline, reformulated gasoline, biogasoline (i.e., gasoline which in some way is derived from biomass), Fischer-Tropsch gasoline, and mixtures thereof. Additionally, the term "gasoline" includes a gasoline blend, gasoline blends, blended gasoline, a gasoline blend stock, gasoline blend stocks, and mixtures thereof. It is understood that the specific components and allowances of suitable gasolines can vary based on seasonal and regional guidelines.

The terms "gasoline blend" and "blended gasoline" as used herein, refer to a mixture containing at least a gasoline and/or gasoline subgrade and one or more alcohols. A gasoline blend includes, but is not limited to, an unleaded gasoline suitable for combustion in an automotive engine.

The terms "American Society for Testing and Materials" and "ASTM" as used herein, refer to the international standards organization that develops and publishes voluntary consensus technical standards for a wide range of materials, products, systems, and services, including fuels.

The term "octane rating" as used herein, refers to the measurement of the resistance of a fuel to auto-ignition in spark ignition internal combustion engines or to the measure of a fuel's tendency to burn in a controlled manner. An octane rating can be a research octane number (RON) or a motor octane number (MON). RON refers to the measurement determined by running the fuel in a test engine with a variable compression ratio under controlled conditions, and comparing the results with those for mixtures of iso-octane and n-heptane. MON refers to the measurement determined using a similar test to that used in RON testing, but with a preheated fuel mixture, a higher engine speed, and ignition timing adjusted depending on compression ratio. RON and MON are determined by standard test procedures described in the ASTM D2699 and ASTM D2700, respectively.

The fuel classes described herein are defined by the specifications for gasolines set forth in ASTM D 4814 and EN228 and vary based on a number of parameters affecting volatility and combustion such as weather, season, geographic location and altitude. Gasolines produced in accordance with ASTM D 4814 are broken into vapor pressure/distillation classes AA, A, B, C, D and E, and vapor lock protection classes 1, 2, 3, 4, 5, and 6, each class having a set of specifications describing gasolines meeting the requirements of the respective classes. Gasolines produced in accordance with EN228 are broken into volatility classes A, B, C/C1, D/D1, E/E1, and F/F1, each class having a set of specifications describing gasolines meeting the requirement of the respective classes.

The total weighted demerits of a gasoline blend is a measurement of cold start and warm up driveability performance according to the Coordinating Research Council (CRC) Cold-Start and Warm-up Driveability Procedure CRC Designation E-28-94. In this procedure, the vehicle is driven from a cold start through a set of acceleration/deceleration maneuvers by a trained rater who gives a severity rating (trace, moderate, heavy, extreme) to any driveability malfunctions observed during the maneuvers (stall, idle roughness, backfire, hesitation, stumble, surge). The severity ratings are used to calculate a total weighted demerit (TWD) for the vehicle at the test condition. The higher the TWD value, the poorer the CS&W driveability performance of the gasoline blend.

Gasolines are well-known in the art, and generally contain as a primary component a mixture of hydrocarbons having different boiling points that typically boil at a temperature in the range of from about 79° F. to about 437° F. under atmospheric pressure. This range is approximate and can vary depending upon the actual mixture of hydrocarbon molecules present, the additives or other compounds present (if any), and the environmental conditions. Oxygenated gasolines are blends of one or more gasoline blend stocks and one or more oxygenates. Oxygenates are compounds or mixtures of compounds that comprise about 99 weight percent of carbon, hydrogen and oxygen, with oxygen comprising at least about 5 weight percent thereof. Typical oxygenates are alcohols, ethers and mixtures thereof.

Gasoline blend stocks can be produced from a single component, such as the product from a refinery alkylation unit or other refinery streams. However, gasoline blend stocks are more commonly blended using more than one component. Gasoline blend stocks are combined to make gasolines that meet desired physical and performance characteristics and meet regulatory requirements, and may involve a few blending components. For example, a gasoline blending stock may have two to four blending components, or may have numerous blending components, such as more than four components.

Gasolines and gasoline blend stocks optionally may include other chemicals or additives. For example, additives or other chemicals can be added to adjust properties of a gasoline to meet regulatory requirements, add or enhance desirable properties, reduce undesirable detrimental effects, adjust performance characteristics, or otherwise modify the characteristics of the gasoline. Examples of such chemicals or additives include detergents, antioxidants, stability enhancers, demulsifiers, corrosion inhibitors, metal deactivators, and others. More than one additive or chemical can be used.

The term "adjusting" as used herein includes changing concentrations of the components, eliminating components, adding components, or any combination thereof so as to modify the boiling characteristics/volatility.

Useful additives and chemicals are described in Colucci et al., U.S. Pat. No. 5,782,937, which is incorporated herein by reference. Such additives and chemicals are also described in Wolf, U.S. Pat. No. 6,083,228, and Ishida et al., U.S. Pat. No. 5,755,833, both of which are incorporated by reference herein. Gasolines and gasoline blend stocks may also contain solvents or carrier solutions which are often used to deliver additives into a fuel. Examples of such solvents or carrier solutions include, but are not limited to, mineral oil, alcohols, aromatic naphthas, synthetic oils, and numerous others which are known in the art.

Gasoline blend stocks suitable for use in the method of this invention are typically blend stocks useful for making gasolines for consumption in spark ignition engines or in other engines which combust gasoline. Suitable gasoline blend stocks also include blend stocks having low sulfur content which may be desired to meet regional requirements, for example, having less than about 150, less than about 140, less than about 130, less than about 120, less than about 110, less than about 100, less than about 90, less than about 80, less than about 70, less than about 60, less than about 50, less than about 40, or less than about 30 parts per million parts by weight of sulfur. Such suitable gasoline blend stocks also include blend stocks having low aromatics content which may be desirable to meet regulatory requirements, for example having less than about 8000, less than about 7750, less than about 7500, less than about 7250, or less than about 7000 parts per million parts by volume of benzene, or, for example, having less than about 35, less than about 34, less than about 33, less than about 32, less than about 31, less than about 30, less than about 29, less than about 28, less than about 27, less than about 26, or less than about 25 volume percent total of all aromatic species present.

An oxygenate such as ethanol can also be blended with the gasoline blending stock. In that case, the resulting gasoline blend includes a blend of one or more gasoline blending stocks and one or more other suitable oxygenates. In another embodiment, one or more butanol isomers can be blended with one or more gasoline blending stocks and, optionally, with one or more suitable oxygenates such as ethanol. In such embodiment, one or more gasoline blend stocks, one or more butanol isomers and optionally one or more other suitable oxygenates can be blended in any order. For further examples, a butanol, such as isobutanol, n-butanol, or tert-butanol, can be added with the other suitable oxygenates, added before the other suitable oxygenates or blended with the other suitable oxygenates before being added to a gasoline blend stock. As another example, one or more other suitable oxygenates and a butanol can be added in several different locations or in multiple stages. For further examples, a butanol, such as isobutanol, can be added with the other suitable oxygenates, added before the other suitable oxygenates or blended with the other suitable oxygenates before being added to a gasoline blend stock. In one embodiment, a butanol, such as isobutanol, is added to oxygenate gasoline. In another embodiment, one or more other suitable oxygenates and a butanol can be blended into a gasoline blend stock contemporaneously.

In any such embodiment one or more butanol isomers and optionally one or more other suitable oxygenates can be added at any point within the distribution chain. For example, a gasoline blend stock can be transported to a terminal, and then a butanol and optionally one or more other suitable oxygenates can be blended with the gasoline blend stock, individually or in combination, at the terminal. As a further example, the one or more gasoline blending stocks, one or more butanol isomers and optionally one or more other suitable oxygenates can be combined at a refinery. Other components or additives can also be added at any point in the distribution chain. Furthermore, the method of the present invention can be practiced at a refinery, terminal, retail site, or any other suitable point in the distribution chain.

In an embodiment of the invention, the total weighted demerits of the gasoline blend is below about 40, below about 35, below about 30, below about 25, below about 20, below about 15, or below about 10.

When butanol is included into many probable gasoline/butanol blends that would otherwise appear to meet current ASTM and EU volatility specification limits, the cold-start and warm-up (CS&W) driveability performance can be significantly deteriorated. However, it has been surprisingly and unexpectedly found that the negative deterioration associated with CS&W driveability performance when butanol is included in gasoline/butanol blends is avoided by the methods described herein.

In particular, fifteen ASTM A-class fuels with isobutanol concentrations ranging from zero to 24 volume percent were tested for volatility properties and CS&W performance using industry standard methods (for example, ASTM standard distillation and vapor pressure fuel inspection tests, CRC E28 standard cold-start and warm-up driveability tests). All fifteen fuels were tested for CS&W performance in each of 12 light duty vehicles at 40° F., and one-third of the tests were replicated to gain statistical power. A total of 240 CS&W evaluations (20 on each vehicle) were conducted. The results of these tests are presented in Tables 1 and 2 below.

These tests were patterned after a similar program conducted by the Coordinating Research Council (CRC Program CM-138-02, documented as CRC Report No. 638); the objective of the CRC Program was to establish the volatility/composition effect of low-ethanol (less than 10 volume percent) gasolines on CS&W driveability. The subject CRC Program established that Equation 1 above, wherein an ethanol "offset" term was added to the prior definition of ASTM driveability index, DI, does describe the CS&W driveability performance of gasoline blends that contain such low concentrations of ethanol. FIG. 1 is a plot of the mean corrected natural logarithm of total weighted demerits for a number of blends of low concentrations of isobutanol in gasoline versus the ASTM DIs for those blends. FIG. 1 presents driveability results for the low butanol fuels tested and indexed using Equation 1. As is evident, both graphically and from the calculated fit statistic, $R^2$, Equation 1 fails to describe the CS&W driveability performance of the low-butanol fuels.

The mean corrected natural logarithms of the total weight demerits (TWD) in the figures are calculated from the fleet data for all of the CS&W tests. They represent an unbiased average performance of a fuel in the 12 vehicle fleet employed. All 15 fuel and 12 vehicle combinations total 180 tests that were performed. However, 60 additional tests that were replicates of some of the 180 tests were also performed. Thus, a total of 240 tests were performed. The corrected mean is the least squares mean of each fuel that is balanced as though the same number of tests were performed on each fuel-vehicle combination. This affords an unbiased TWD for each fuel averaged over the 12 vehicles.

The following extension/modification was made to the customary driveability index DI presented as Equation 1. Equations 2a and 2b below present the Low-Butanol Driveability Index or LBDI, which is a modification of the ASTM DI, and is a linear combination of temperatures, alcohol concentrations and E200.

$$\text{LBDI} = a_1 T_{10} + a_2 T_{50} + a_3 T_{90} + a_4 \text{EtOH} + \text{BuOH}(a_5 - a_6 \text{E200}) \quad \text{(Eq. 2a)}$$

wherein LBDI is the modified driveability index; $T_{10}$, $T_{50}$, and $T_{90}$ are the temperatures for distillation of 10, 50 and 90 volume percent, respectively, of the blend; EtOH and BuOH are the volume percents of ethanol and butanol, respectively, in the blend; E200 is the volume percent of the blend that distills at temperatures up to 200° F.; and $a_1$, $a_2$, $a_3$, $a_4$, $a_5$ and $a_6$ are coefficients selected to afford a substantially linear relationship between the values of the aforesaid linear combination for gasoline blends containing butanol and optionally ethanol and the logarithms of the mean measured total weighted demerits for such blends, at concentrations of ethanol less than 20 volume percent, less than 19 volume percent, less than 18 volume percent, less than 17 volume percent, less than 16 volume percent, less than 15 volume percent, less than 14 volume percent, less than 13 volume percent, less than 12 volume percent, less than 11 volume percent, less than 10 volume percent, less than 9 volume percent, less than 8 volume percent, less than 7 volume percent, less than 6 volume percent, or less than 5 volume percent, at concentrations of butanol less than 30 volume percent, less than 29 volume percent, less than 28 volume percent, less than 27 volume percent, less than 26 volume percent, less than 25 volume percent, less than 24 volume percent, less than 23 volume percent, less than 22 volume percent, less than 21 volume percent, less than 20 volume percent, less than 19 volume percent, less than 18 volume percent, less than 17 volume percent, less than 16 volume percent, less than 15 volume percent, less than 14 volume percent, less than 13 volume percent, less than 12 volume percent, less than 11 volume percent, less than 10 volume percent, less than 9 volume percent, less than 8 volume percent, less than 7 volume percent, less than 6 volume percent, or less than 5 volume percent, and at total concentrations of ethanol and butanol less than 35 volume percent, less than 30 volume percent, less than 25 volume percent, less than 20 volume percent, less than 15 volume percent, less than 10 volume percent. In one embodiment, the blend is ethanol-free.

In one embodiment, the low butanol driveability index (LBDI) can be determined before blending the gasoline, the at least one biologically-sourced butanol isomer, and optionally ethanol to form the butanol gasoline blend. In another embodiment, the low butanol driveability index (LBDI) can be determined after blending the gasoline, the at least one biologically-sourced butanol isomer, and optionally ethanol to form the butanol gasoline blend. If the LBDI is determined afterwards, the gasoline amount, the at least one biologically-sourced butanol isomer amount, the ethanol, or any combination thereof, can optionally be adjusted so that the LBDI has a value equal to the linear combination $a_1 T_{10} + a_2 T_{50} + a_3 T_{90} + a_4 \text{EtOH} + \text{BuOH}(a_5 - a_6 \text{E200})$ below the maximum limit for Driveability Index (DI) for the specific class of gasoline. In yet another embodiment, the low butanol driveability index (LBDI) can be determined during blending the gasoline, the at least one biologically-sourced butanol isomer, and optionally ethanol to form the butanol gasoline blend. If the LBDI is determined during blending, the gasoline amount, the at least one biologically-sourced butanol isomer amount, the ethanol, or any combination thereof, can optionally be adjusted so that the LBDI has a value equal to the linear combination $a_1 T_{10} + a_2 T_{50} + a_3 T_{90} + a_4 \text{EtOH} + \text{BuOH}(a_5 - a_6 \text{E200})$ below the maximum limit for Driveability Index (DI) for the specific class of gasoline. Of course, the low butanol driveability index (LBDI) can be determined once or more than once, and can be determined at various stages of blending the butanol gasoline blend, including, but not limited to, before, during, and after the butanol gasoline blend is produced.

When the concentration of ethanol is less than 10 volume percent, $a_1$, $a_2$, $a_3$, and $a_4$, equal approximately 1.5, 3, 1, and 2.4, respectively, and Equation 2a becomes:

$$\text{LBDI} = 1.5 T_{10} + 3 T_{50} + T_{90} + 2.4 \text{EtOH} + \text{BuOH}(a_5 - a_6 \text{E200}) \quad \text{(Eq. 2b)}$$

Furthermore, when the concentration of ethanol is less than 10 volume percent and the concentration of butanol is less than 20 volume percent, $a_1$, $a_2$, $a_3$, $a_4$, $a_5$ and $a_6$ equal approximately 1.5, 3, 1, 2.4, 16 and 0.3, respectfully, and Equations 2a and 2b become:

$$\text{LBDI} = 1.5 T_{10} + 3 T_{50} + T_{90} + 2.4 \text{EtOH} + \text{BuOH}(16 - 0.3 \text{E200}) \quad \text{(Eq. 2c)}$$

or in other words:

$$\text{LBDI} = \text{DI} + \text{BuOH}(16 - 0.3 \text{E200}) \quad \text{(Eq. 2d)}$$

wherein DI is the aforesaid ASTM DI. As seen from the form of the equation, LBDI collapses to the customary ASTM DI when butanol is absent, and hence the same specification limits established for DI are applicable for LBDI.

In European applications, the EN228 gasoline specification controls mid-range volatility for good CS&W driveability by specifying a minimum value for E100, which is the fuel fraction distilled by 100° C. in the standard distillation test. Testing has also shown that the present specification and limiting value E100 are not applicable for low-butanol gasolines. Consequently, the present invention defines the "Effective E100" as the linear combination:

$$\text{Eff}_{100} = \text{E100} - \text{BuOH}(b_1 - b_2 \text{E100}) \quad \text{(Eq. 3a)}$$

Where $\text{Eff}_{100}$ is the new modified driveability index designated "Effective E100"; E100 is the fuel volume percent distilled at 100° C. as observed in the standard distillation test, and BuOH is again the fuel butanol content in volume percent; all three quantities are in units of volume percent; and $b_1$, and $b_2$ are coefficients selected to afford a substantially linear relationship between the values of the aforesaid linear combination for gasoline blends containing butanol and optionally ethanol and the natural logarithms of the mean measured total weighted demerits for such blends, at concentrations of ethanol less than 20 volume percent, less than 19 volume percent, less than 18 volume percent, less than 17 volume percent, less than 16 volume percent, less than 15 volume percent, less than 14 volume percent, less than 13 volume percent, less than 12 volume percent, less than 11 volume percent, less than 10 volume percent, less than 9 volume percent, less than 8 volume percent, less than 7 volume percent, less than 6 volume percent, or less than 5 volume percent, at concentrations of butanol less than 30 volume percent, less than 29 volume percent, less than 28 volume percent, less than 27 volume percent, less than 26 volume percent, less than 25 volume percent, less than 24 volume percent, less than 23 volume percent, less than 22 volume percent, less than 21 volume percent, less than 20 volume percent, less than 19 volume percent, less than 18 volume percent, less than 17 volume percent, less than 16 volume percent, less than 15 volume percent, less than 14 volume percent, less than 13 volume percent, less than 12 volume percent, less than 11 volume percent, less than 10 volume percent, less than 9 volume percent, less than 8 volume percent, less than 7 volume percent, less than 6 volume percent, or less than 5 volume percent, and at total concentrations of ethanol and butanol less than 35 volume percent, less than 30 volume percent, less than 25 volume percent, less than 20 volume percent, less than 15 volume percent, less than 10 volume percent. In one embodiment, the blend is ethanol-free.

When the concentration of ethanol is less than 5 volume percent and the concentration of butanol is less than 20 volume percent, $b_1$ and $b_2$ equal approximately 2.3 and 0.034, respectively, and Equation 3a becomes:

$$\text{Eff}_{100} = \text{E100} - \text{BuOH}(2.3 - 0.034 \text{E100}) \quad \text{(Eq 3b)}$$

Once again, the new index $Eff_{100}$ reverts to the customary form when butanol is absent, and hence the existing limiting values established for E100 are applicable for $Eff_{100}$.

In each case, the index is employed by inserting distillation test data for a subject fuel in the equation and calculating the value of the new index. For LBDI, the resulting value calculated from Eq. 2a-2c is then compared to the specification maximum limit for DI given for that class of fuel as specified in Table 1 of ASTM D 4814-08a. If the calculated LBDI is below the specified DI maximum for the appropriate volatility class, the fuel will have acceptable CS&W performance. Similarly for $Eff_{100}$, the value calculated from the test data in Eq. 3a-3b is compared to the minimum E100 value for that class of fuel as specified in Table 2 in EN 228. If the calculated value of $Eff_{100}$ is above the specified minimum for E100 for the appropriate volatility class, the fuel will have acceptable CS&W performance.

Figure 2:
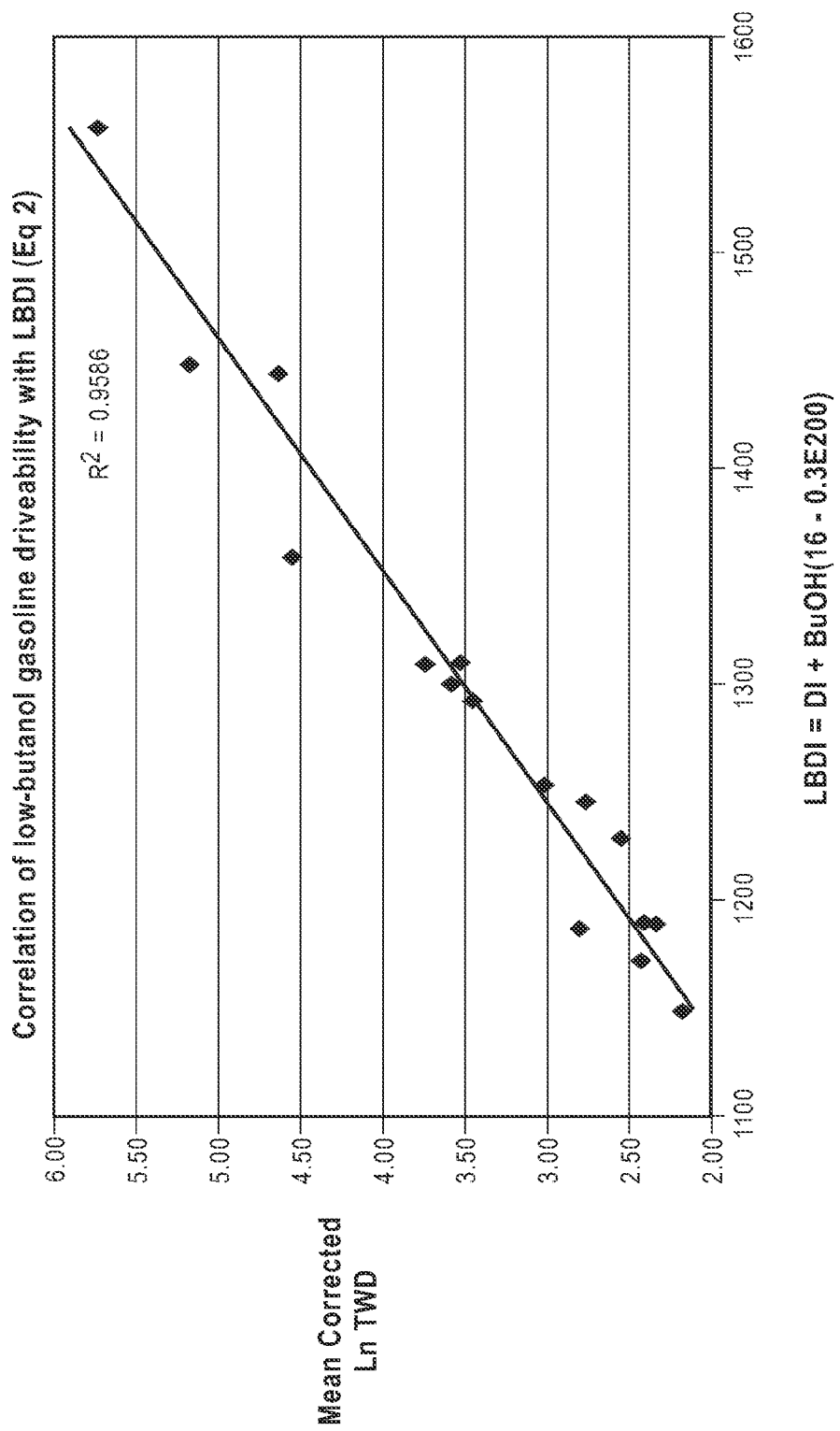
FIG. 2 is a plot of the mean corrected natural logarithm of total weighted demerits of low butanol gasoline driveability versus LBDI.

Eqs. 2a-2d and 3a-3b are significantly more effective than Eq. 1 in correlating the CS&W driveability results for the low butanol fuels as shown in FIGS. 2 and 3. FIGS. 2 and 3 establish the efficacy of Eqs. 2a-2d and 3a-3b, respectively, in describing the CS&W driveability performance of low-butanol gasolines from volatility and composition properties. To demonstrate that the current specification limits from ASTM D 4814 and EN 228 are appropriate for the new indices, the data of FIGS. 2 and 3 are re-plotted without the log transform in FIGS. 4 and 5, respectively. These plots also differ in that specific symbols have been assigned to indicate the butanol concentrations of the fuels tested.

The data in FIG. 4 span the iso-butanol concentrations up to 24 volume percent, include the 0 volume percent i-BuOH conventional fuels as reference points, and also span the range of driveability performance from acceptable to unacceptable. Conventional fuels both below and above the DI limit of 1250 are included. Because the variable ranges are so complete, it can be concluded that the present limit of 1250 maximum DI for A-class fuels is also appropriate for fuels that contain up to 24 volume percent of isobutanol when LBDI is used as the index. It is readily apparent that the fuels containing up to 24 volume percent of isobutanol can be formulated using 1250 LBDI as a limit and achieve the same low demerit level as conventional butanol-free fuels indexed to 1250 DI. Similarly, butanol fuels with LBDI over 1250 have higher, unacceptable levels of demerits just as do the conventional butanol-free fuels with DI over 1250.

Similar conclusions can be reached for the European style specifications and indices from FIG. 5. Data for the complete range of butanol-containing and butanol-free fuels again span the range of driveability performance from acceptable (conventional fuels with E100 above 46 volume percent) to unacceptable (conventional fuels with E100 below 46 volume percent). FIG. 5 shows that when iso-butanol fuels are blended to $Eff_{100}$ greater than or equal to 46 volume percent, the driveability demerits are just as low as conventional butanol-free fuels blended to the established limit of E100 greater than or equal to 46 volume percent. The data also suggest that the established limit of minimum 46 volume percent may be overly restrictive, as it is apparent that both conventional and butanol-containing fuels with $Eff_{100}$ as low as 40 volume percent or so also exhibit very low driveability demerits.

According to the invention, FIGS. 2 and 3 can also be used to calculate the TWD of a new gasoline blend comprising butanol, and optionally ethanol. The method would involve blending gasoline with butanol and optionally, ethanol; measuring the E200, $T_{10}$, $T_{50}$, and $T_{90}$ values of the gasoline blend, inputting the E200, $T_{10}$, $T_{50}$, and $T_{90}$ values in the equation $a_1T_{10}+a_2T_{50}+a_3T_{90}+a_4EtOH+BuOH$ ($a_5-a_6E200$) to calculate LBDI of the fuel blend using the appropriate equation 2a-d above, and correlating the LBDI value of the fuel blend using FIG. 2 to calculate a TWD for the gasoline blend. The calculated TWD of the gasoline blend can be used to predict the cold-start and warm-up driveability performance of the fuel.

The data from which the plots in FIGS. 2 and 3 were made are presented in Tables 1 and 2, respectively. Fuels for which TWD's are up to about 20 are considered to afford acceptable driveability characteristics. The data in Table 1 suggest inaccurately that the DIs of fuels 3, 4, 6, 7, 9, 13 and 18 would afford acceptable driveability characteristics, but their LBDIs indicate to the contrary that their driveability characteristics are unacceptable or, in one case, only borderline. The data in Table 2 suggests inaccurately that the E100s of fuels 3, 4, 6, 7, and 18 would afford acceptable driveability characteristics, but the Eff100's indicate to the contrary that they are unacceptable, or in one case, only borderline.

TABLE 1

| Fuel | class A, DI | % i-BuOH | T10° F. | T50° F. | T90° F. | E200, vol % | DI | LBDI | TWD |
|---|---|---|---|---|---|---|---|---|---|
| 0 | 1250 | 0 | 128.65 | 217.9 | 343.7 | 43.05 | 1190 | 1190 | 10 |
| 1 | 1250 | 0 | 136.5 | 231.5 | 345.8 | 33.7 | 1245 | 1245 | 15 |
| 2 | 1250 | 0 | 152.45 | 240.7 | 359.05 | 22.35 | 1310 | 1310 | 32 |
| 3 | 1250 | 16 | 151.7 | 209.2 | 332 | 31.5 | 1187 | 1292 | 34.9 |
| 4 | 1250 | 16 | 148.8 | 213.2 | 370.1 | 28.7 | 1233 | 1351 | 93 |
| 5 | 1250 | 16 | 162.3 | 226.4 | 361.8 | 20.9 | 1284 | 1440 | 174.3 |
| 6 | 1250 | 24 | 139.7 | 208.3 | 344.4 | 36.6 | 1179 | 1299 | 33 |
| 7 | 1250 | 24 | 152.8 | 213.6 | 365.8 | 26.1 | 1236 | 1432 | 103.8 |
| 8 | 1250 | 24 | 170.4 | 221.6 | 376.5 | 18.4 | 1297 | 1548 | 305 |
| 9 | 1250 | 8 | 148.25 | 225.9 | 337.65 | 31.45 | 1238 | 1290 | 30 |
| 10 | 1250 | 0 | 128.65 | 217.9 | 343.7 | 43.05 | 1190 | 1190 | 10.7 |
| 11 | 1250 | 0 | 152.45 | 240.7 | 359.05 | 22.35 | 1310 | 1310 | 41.2 |
| 13 | 1250 | 8 | 148.25 | 225.9 | 337.65 | 31.45 | 1238 | 1290 | 30 |
| 14 | 1250 | 0 | 131 | 207.2 | 331.6 | 46.5 | 1150 | 1150 | 8.3 |
| 15 | 1250 | 16 | 133 | 202.3 | 331.9 | 48.3 | 1138 | 1162 | 10.8 |
| 16 | 1250 | 24 | 135.8 | 205.9 | 331.9 | 44.9 | 1153 | 1214 | 12.3 |
| 17 | 1250 | 16 | 145.6 | 201.9 | 321.4 | 46.7 | 1146 | 1177 | 16 |
| 18 | 1250 | 16 | 136.4 | 209.3 | 357.4 | 41.9 | 1190 | 1245 | 19 |

TABLE 2

| Fuel | class A, E100 spec | i-BuOH, vol % | E70, vol % | E100 | Eff100 | TWD |
|---|---|---|---|---|---|---|
| 0 | 46 min | 0 | 25.1 | 47.7 | 47.7 | 10.1 |
| 1 | 46 min | 0 | 17.6 | 39.4 | 39.4 | 15.6 |
| 2 | 46 min | 0 | 11.15 | 28.5 | 28.5 | 32.9 |
| 3 | 46 min | 16 | 11.5 | 53.9 | 46.4 | 34.9 |
| 4 | 46 min | 16 | 12 | 48.0 | 37.4 | 93.3 |
| 5 | 46 min | 16 | 9.2 | 34.4 | 16.4 | 174.3 |
| 6 | 46 min | 24 | 15.3 | 57.4 | 49.0 | 33.7 |
| 7 | 46 min | 24 | 11 | 46.1 | 28.5 | 103.8 |
| 8 | 46 min | 24 | 7.9 | 31.3 | 1.6 | 305.2 |
| 9 | 46 min | 8 | 12.4 | 41.6 | 34.5 | 30.2 |
| 10 | 46 min | 0 | 25.1 | 47.7 | 47.7 | 10.7 |
| 11 | 46 min | 0 | 11.15 | 28.5 | 28.5 | 41.2 |
| 13 | 46 min | 8 | 12.4 | 41.6 | 34.5 | 30.9 |
| 14 | 46 min | 0 | 26.1 | 52.5 | 52.5 | 8.3 |
| 15 | 46 min | 16 | 22.5 | 58.9 | 54.2 | 10.8 |
| 16 | 46 min | 24 | 20.4 | 57.8 | 49.8 | 12.3 |
| 17 | 46 min | 16 | 16 | 62.9 | 60.3 | 16.1 |
| 18 | 46 min | 16 | 18.9 | 53.5 | 45.9 | 19.8 |

The general method to determine the coefficients a1 through a6 for the full range of ethanol concentrations up to 20 volume percent and butanol concentrations up to 34 volume percent is similar to that used to determine the ethanol offset by the CRC program (CRC Program CM-138-02, CRC Report No. 638) referenced hereinabove. This method involves developing a regression equation relating a natural logarithm of TWD measured by the CRC E28 standard CS&W test to corresponding fuel variables. To achieve collapse of this equation to the standard DI equation the coefficients a1 through a4 were chosen to be the same as those used in the ASTM D 4814 DI equation. The additional fuel variables E200 and iBuOH were added to give a correlation that fit the data within the variability of the test method, and their values were calculated according to the least squares method using a general linear statistical model. In particular, the iBuOH content was added as a linear term and E200 added as an interaction term (i.e. iBuOH*E200). FIG. 2 shows the good correlation for this semi-logarithmic relation. Coefficients for other butanol isomers may be derived by performing CS&W tests using fuels containing the isomer of interest at various concentrations and statistically analyzing the results (i.e. natural logarithm of TWD) using a general linear statistical model with factors: DI, butanol isomer concentration and E200*butanol isomer concentration.

Similarly, coefficients for the European version of the equation, $b_1$, and $b_2$ are estimated by statistically analyzing the natural logarithm TWD as a function of E100, butanol isomer concentration, and E100* butanol isomer concentration using a general linear model. FIG. 3 shows the results of this semi-logarithmic correlation.

Those skilled in the art would readily appreciate that if other measures of the volatility or boiling point profile, such as $T_{20}$, $T_{30}$, E158 or E70, of a gasoline blend were employed instead of $T_{10}$, $T_{50}$, $T_{90}$, E200 or E100, this would result in relatively minor variations of Equations 2(a)-2(d) and 3(a)-3(b), but the claimed method and gasoline blend of this invention includes such variations.

Tables 3 and 4 contain data from driveability tests similar to those employed for that data in Tables 1 and 2. The fuels employed were of volatility classes AA and E and were either gasoline only or blends of gasoline with either ethanol alone, isobutanol alone or both ethanol and isobutanol. In Table 3 for fuels that were gasoline alone or blends of gasoline and only ethanol, the DIs and LBDIs were equal. For fuels that were blends of gasoline with either butanol alone or both butanol and ethanol, the LBDIs were larger than the DIs, and generally the closer the LBDIs approached the specified maximum for the D 4814 DI, the greater the number of demerits. In Table 4, the E100s and $Eff_{100}$s were equal for fuels that were either gasoline alone or blends of gasoline with ethanol alone. The $Eff_{100}$s were generally smaller than the E100s for fuels that were blends of gasoline with either butanol alone or both butanol and ethanol. $Eff_{100}$s below or closer to the specified minimum for E100 generally had a greater number of demerits.

TABLE 3

| Fuel ID | D4814 Volatility Class | D4814 DI spec, F | % i-BuOH | % EtOH | T10, °F. | T50, °F. | T90, °F. | E200 vol % | DI | LBDI | Driveability Demerits |
|---|---|---|---|---|---|---|---|---|---|---|---|
| AA-0 | AA | 1250 max | 0 | 0 | 158.4 | 224.9 | 351.4 | 34.7 | 1264 | 1264 | 11.5 |
| AA-1 | AA | 1250 max | 0 | 10 | 137.3 | 211.2 | 341.6 | 46.2 | 1205 | 1205 | 11.7 |
| AA-2 | AA | 1250 max | 16 | 0 | 146.7 | 205.6 | 333.8 | 43.6 | 1171 | 1217 | 11.2 |
| AA-3 | AA | 1250 max | 16 | 0 | 146.7 | 208.9 | 347.1 | 41.0 | 1194 | 1253 | 15.0 |
| AA-4 | AA | 1250 max | 0 | 10 | 137.1 | 219.8 | 359.6 | 44.8 | 1249 | 1249 | 14.6 |
| AA-5 | AA | 1250 max | 8 | 5 | 139.7 | 201.5 | 335.3 | 48.9 | 1161 | 1172 | 12.4 |
| AA-6 | AA | 1250 max | 8 | 5 | 140.1 | 206.7 | 353.7 | 46.1 | 1196 | 1213 | 15.3 |
| AA-7 | AA | 1250 max | 0 | 10 | 138.3 | 213.7 | 274 | 44 | 1147 | 1147 | 9.7 |
| AA-9 | AA | 1250 max | 16 | 0 | 152.7 | 201.8 | 288.1 | 46.4 | 1123 | 1156 | 10.4 |
| AA-10 | AA | 1250 max | 8 | 5 | 142.4 | 199.8 | 282.8 | 50.3 | 1108 | 1115 | 10.1 |
| AA-11 | AA | 1250 max | 0 | 0 | 141.9 | 224.6 | 341.8 | 36.9 | 1228 | 1228 | 10.3 |
| E-16 | E | 1200 max | 0 | 10 | 111.6 | 197.3 | 342.3 | 50.4 | 1126 | 1126 | 15.5 |
| E-17 | E | 1200 max | 16 | 0 | 110 | 206 | 319.9 | 45.6 | 1103 | 1140 | 15.4 |
| E-18 | E | 1200 max | 16 | 0 | 108.8 | 194.1 | 306.7 | 54.4 | 1052 | 1047 | 10.6 |
| E-19 | E | 1200 max | 0 | 0 | 98.4 | 205.8 | 343.4 | 48.6 | 1108 | 1108 | 11.0 |
| E-20 | E | 1200 max | 16 | 0 | 109.2 | 208.3 | 335.8 | 43.2 | 1125 | 1173 | 17.8 |

TABLE 4

| Fuel | Volatility Class | EN 228 E100 spec vol % Min | vol % i-BuOH | % EtOH | EN228 E100 vol % | Eff100 vol % | Driveability Demerits |
|---|---|---|---|---|---|---|---|
| AA-0 | AA | 46 | 0 | 0 | 42.6 | 42.6 | 11.5 |
| AA-1 | AA | N/A | 0 | 10 | 50.4 | | 11.7 |

TABLE 4-continued

| Fuel | Volatility Class | EN 228 E100 spec vol % Min | vol % i-BuOH | % EtOH | EN228 E100 vol % | Eff100 vol % | Driveability Demerits |
|---|---|---|---|---|---|---|---|
| AA-2 | AA | 46 | 16 | 0 | 58.2 | 53.1 | 11.2 |
| AA-3 | AA | 46 | 16 | 0 | 52.8 | 44.8 | 15.0 |
| AA-4 | AA | N/A | 0 | 10 | 48.5 | | 14.6 |
| AA-5 | AA | 46 | 8 | 5 | 57.3 | 54.5 | 12.4 |
| AA-6 | AA | 46 | 8 | 5 | 52.7 | 48.6 | 15.3 |
| AA-7 | AA | N/A | 0 | 10 | 49.6 | | 9.7 |
| AA-9 | AA | 46 | 16 | 0 | 70.0 | 71.3 | 10.4 |
| AA-10 | AA | 46 | 8 | 5 | 61.7 | 60.1 | 10.1 |
| AA-11 | AA | 46 | 0 | 0 | 43.1 | 43.1 | 10.3 |
| E-16 | E | N/A | 0 | 10 | 53.2 | | 15.5 |
| E-17 | E | 46 | 16 | 0 | 56.6 | 50.6 | 15.4 |
| E-18 | E | 46 | 16 | 0 | 65.3 | 64.1 | 10.6 |
| E-19 | E | 46 | 0 | 0 | 51.6 | 51.6 | 11.0 |
| E-20 | E | 46 | 16 | 0 | 53 | 45.8 | 17.8 |

It has also been surprisingly and unexpectedly found that the LBDI of a gasoline blend with a biologically-sourced butanol isomer and optionally ethanol can be maintained below, or reduced to a level below, the specified maximum for that class of gasoline by adding a sufficient volume of a light hydrocarbon to the blend. Such light hydrocarbons serve to modify the boiling temperature distribution of the blend so as to improve evaporation/combustibility of the fuel in a cold engine. Some refinery streams that could be employed as such light hydrocarbons are listed in Table 5. Examples of this use are hydrocarbons used form azeotropes with the oxygenates in the gasoline blend, namely, butanol isomers and ethanol. Such azeotropes boil at even lower temperatures than the specific hydrocarbon which is added to the blend and which is a component of the azeotrope. Thus, the added light hydrocarbon that forms the azeotrope has a greater effect in of reducing the boiling point of the blend than would be expected from the boiling point of the added hydrocarbon itself. Suitable such hydrocarbons and the boiling points of their azeotropes with ethanol and each butanol isomer is shown in Table 6. The word "zeotrope" in Table 6 indicates that no azeotrope was formed. In Table 6, Wt. % is the weight percent of the hydrocarbon in the azeotrope. In one embodiment, the light hydrocarbons can comprise from 5 to 9 carbon atoms, and can comprise either at least one refinery stream having T90s less than 260° F., the refinery stream comprising paraffins, cycloparaffins, olefins or aromatic compounds or mixtures thereof, or the light hydrocarbons can comprise at least one hydrocarbon that forms azeotropes with butanol or ethanol, if ethanol present, which boil at or below 216° F., or the light hydrocarbon can comprise mixtures and combinations thereof.

TABLE 5

| | Approximate Distillation, ° F. | | | |
|---|---|---|---|---|
| Stream Name | T10 | T50 | T90 | Major Chemical types |
| Isomerate | 116 | 130 | 160 | branched C5-C6 paraffins |
| Light virgin naphtha | 95 | 130 | 180 | C5-C8 paraffins, cycloparaffins, olefins, aromatics |
| Light straight run naphtha | 95 | 130 | 180 | C5-C8 paraffins, cycloparaffins, olefins, aromatics |
| Light catalytically cracked naphtha | 110 | 140 | 250 | C5-C8 paraffins, cycloparaffins, olefins, aromatics |
| Light hydrocracked naphtha | 110 | 130 | 175 | C5-C8 paraffins, cycloparaffins, aromatics |
| Light hydrotreated coker naphtha | 115 | 140 | 200 | C5-C8 paraffins, cycloparaffins, aromatics |
| Light hydrotreated naphtha | 115 | 140 | 200 | C5-C8 paraffins, cycloparaffins, aromatics |
| Light alkylate | 165 | 215 | 230 | C6-C9 branched paraffins |
| Light reformate | 150 | 190 | 240 | C7-C8 aromatics |
| Raffinate | 150 | 180 | 240 | C6-C9 paraffins, cycloparaffins |

TABLE 6

| Hydrocarbon | Hydrocarbon Boiling Pt. (° C.) | Azeotrope with Isobutanol | | Azeotrope with n-butanol | | Azeotrope with 2-butanol | | Azeotrope with t-butanol | | Azeotrope with ethanol | |
|---|---|---|---|---|---|---|---|---|---|---|---|
| | | B. Pt. (° C.) | Wt. % | B. Pt. (° C.) | Wt. % | B. Pt. (° C.) | Wt. % | B. Pt. (° C.) | Wt. % | B. Pt. (° C.) | Wt. % |
| n-pentane | 36.1 | | | | | | | | | 34.3 | 95 |
| cyclopentane | 36.15 | | | | | | | | | 44.7 | 92.5 |
| n-hexane | 68.9 | 68.3 | 97.5 | 68.2 | 96.8 | | | 63.7 | 78 | 58.68 | 79 |
| methyl cyclopentane | 72 | 71 | 95 | | | 69.7 | 88.5 | 66.6 | 74 | | |
| benzene | 80.1 | 79.3 | 92.6 | zeotrope | | 78.5 | 84.6 | 73.95 | 63.4 | 67.9 | 68.3 |
| cyclohexane | 80.75 | 78.3 | 86 | 79.8 | 90.5 | 76 | 82 | 71.2 | 65.8 | 64.8 | 70.8 |
| cyclohexene | 82.7 | 80.5 | 85.8 | 82 | 95 | | | | | | |
| n-heptane | 98.45 | 90.8 | 73 | 93.85 | 82 | 88.1 | 63.3 | 78 | 38 | | |
| 2,2,4-trimethyl pentane | 99.3 | 92 | 73 | | | | | 88 | 66.2 | | |

TABLE 6-continued

| Hydrocarbon | Hydrocarbon Boiling Pt. (° C.) | Azeotrope with Isobutanol | | Azeotrope with n-butanol | | Azeotrope with 2-butanol | | Azeotrope with t-butanol | | Azeotrope with ethanol | |
|---|---|---|---|---|---|---|---|---|---|---|---|
| | | B. Pt. (° C.), | Wt. % | B. Pt. (° C.) | Wt. % | B. Pt. (° C.) | Wt. % | B. Pt. (° C.) | Wt. % | B. Pt. (° C.) | Wt. % |
| methyl cyclohexane | 100.8 | 92.6 | 68 | 95.3 | 80 | 89.7 | 61.8 | 78.8 | 34 | | |
| 2,5-dimethyl hexane | 109.2 | 98.7 | 58 | | | | | 81.5 | 23 | | |
| toluene | 110.7 | 101.2 | 55 | 105.5 | 72.2 | 95.3 | 45 | zeotrope | | 76.7 | 32 |
| cis-1,3-dimethyl cyclohexane | 120.7 | 102.2 | 44 | | | | | | | | |
| n-octane | 125.75 | | | 108.45 | 54.8 | | | | | 77 | 22 |
| ethyl benzene | 136.15 | 107.2 | 20 | 115.85 | 34.9 | | | | | zeotrope | |
| p-xylene | 138.4 | 107.1 | 11.4 | 115.7 | 32 | | | zeotrope | | zeotrope | |
| m-xylene | 139 | | | 116.5 | 28.5 | | | | | | |
| o-xylene | 143.6 | | | 116.8 | 25 | | | | | | |
| n-nonane | 150.7 | | | 115.9 | 28.5 | | | | | | |

It will be appreciated by those skilled in the art that although the present invention has been described herein by reference to specific means, materials and examples, the scope of the present invention is not limited thereto, and extends to all other means and materials suitable for the practice of this invention.

What is claimed:

1. A method for producing a butanol gasoline blend having good cold start and warm-up (CS&W) driveability performance comprising:
   (a) providing at least one biologically-sourced butanol isomer;
   (b) blending the butanol isomer and optionally ethanol with gasoline to form a butanol gasoline blend, the butanol gasoline blend having a vapor pressure corresponding to a specific ASTM D4814 vapor pressure/distillation class of gasoline;
   (c) determining a value of low butanol driveability index (LBDI) for the butanol gasoline blend wherein the LBDI value is determined by the equation: $a_1T_{10}+a_2T_{50}+a_3T_{90}+a_4EtOH+BuOH(a_5-a_6E200)$; wherein:
   $T_{10}$ is the temperature for distillation of 10-volume percent of the butanol gasoline blend;
   $T_{50}$ is the temperature for distillation of 50-volume percent of the butanol gasoline blend;
   $T_{90}$ is the temperature for distillation of 90-volume percent of the butanol gasoline blend;
   EtOH is the concentration in volume percent of ethanol in the butanol gasoline blend;
   BuOH is the concentration in volume percent of the at least one biologically-sourced butanol isomer in the butanol gasoline blend;
   E200 is the volume percent of the butanol gasoline blend that distills at temperatures up to about 200° F.; and
   $a_1$, $a_2$, $a_3$, $a_4$, $a_5$ and $a_6$ are coefficients selected to give a substantially linear relationship between the values of the linear combination for the butanol gasoline blend containing the at least one butanol isomer and optionally ethanol and the logarithms of the mean corrected total weighted demerits from test measurements of CS&W driveability performance for such blends, at concentrations of ethanol less than about 20 volume percent, at concentrations of the at least one biologically-sourced butanol isomer less than about 30 volume percent, and at total concentrations of ethanol and the at least one biologically-sourced butanol isomer less than about 35 volume percent; and wherein the total weighted demerits of the butanol gasoline blend is less than about 40; and
   (d) optionally adjusting the amount of gasoline, the butanol isomer, and the ethanol, or any combination thereof, such that the value of LBDI is below the maximum limit for Driveability Index (DI) for the specific class of gasoline as specified in Table 1 of ASTM D 4814.

2. The method of claim 1, wherein the butanol gasoline blend comprises up to about 27 volume percent of the at least one biologically-sourced butanol isomer, and wherein the renewable components of the butanol gasoline blend are maximized while good CS&W driveability performance are maintained.

3. The method of claim 1, wherein the blend comprises up to about 15 volume percent of ethanol.

4. The method of claim 1, wherein the at least one biologically-sourced butanol isomer is isobutanol.

5. The method of claim 1, wherein the total concentration of ethanol and the at least one biologically-sourced butanol isomer is less than about 30 volume percent of the blend.

6. The method of claim 1, further comprising blending a sufficient volume of light hydrocarbons to adjust the value of LBDI below said maximum limit for DI.

7. The method of claim 1, wherein:
   $a_1$ is about 1.5;
   $a_2$ is about 3;
   $a_3$ is about 1; and
   $a_4$ is about 2.4;
   when the ethanol concentration is less than about 10 volume percent.

8. The method of claim 1, wherein $a_5$ is about 16; and $a_6$ is about 0.3;
   when the at least one biologically-sourced butanol isomer concentration is less than about 20 volume percent.

9. A method for producing a butanol gasoline blend having good cold start and warm-up (CS&W) driveability performance comprising:
   (a) providing at least one biologically-sourced butanol isomer;
   (b) blending the butanol isomer and optionally ethanol with gasoline, to form a butanol gasoline blend, the butanol gasoline blend having a vapor pressure corresponding to a specific EN228 volatility class of gasoline;

(c) determining an $Eff_{100}$ value for the butanol gasoline blend wherein the $Eff_{100}$ value is determined by the equation: $E100-BuOH(b_1-b_2E100)$; wherein BuOH is the concentration in volume percent of the at least one biologically-sourced butanol isomer in the butanol gasoline blend;

E100 is the volume percent of the butanol gasoline blend that distills at temperatures up to about 100° C.; and $b_1$ and $b_2$ are coefficients selected to give a substantially linear relationship between the values of the linear combination for the butanol gasoline blends containing the at least one butanol isomer and optionally ethanol and the logarithms of the mean corrected measured total weighted demerits for such blends, at concentrations of ethanol less than about 20 volume percent, at concentrations of the at least one biologically-sourced butanol isomer less than about 30 volume percent, and at total concentrations of ethanol and the at least one biologically-sourced butanol isomer less than about 35 volume percent, and wherein the total weighted demerits of the butanol gasoline blend is less than about 40;

(d) optionally adjusting the amount of gasoline, the butanol isomer, and the ethanol, or any combination thereof, such that the value of $Eff_{100}$ is above the minimum limit for E100 for that class of gasoline as specified in Table 2 of EN228.

10. The method of claim 9 further comprising blending a sufficient volume of light hydrocarbons to adjust the value of $Eff_{100}$ above the minimum limit for E100.

11. The method of claim 9, wherein $b_1$ is about 2.3; and $b_2$ is about 0.034;

when the at least one biologically-sourced butanol isomer concentration is less than about 20 volume percent.

12. The method of claim 1 further comprising determining the low butanol driveability index (LBDI) before blending the gasoline, the at least one biologically-sourced butanol isomer, and optionally ethanol to form the butanol gasoline blend.

13. The method of claim 1 further comprising determining the low butanol driveability index (LBDI) after blending the gasoline, the at least one biologically-sourced butanol isomer, and optionally ethanol to form the butanol gasoline blend; and optionally, adjusting the gasoline amount, the at least one biologically-sourced butanol isomer amount, the ethanol, or any combination thereof, so that the LBDI has a value equal to the linear combination $a_1T_{10}+a_2T_{50}+a_3T_{90}+a_4EtOH+BuOH(a_5-a_6E200)$ below the maximum limit for Driveability Index (DI) for the specific class of gasoline.

14. The method of claim 1 further comprising determining the low butanol driveability index (LBDI) during blending the gasoline, the at least one biologically-sourced butanol isomer, and optionally ethanol to form the butanol gasoline blend; and optionally, adjusting the gasoline amount, the at least one biologically-sourced butanol isomer amount, the ethanol, or any combination thereof, so that the LBDI has a value equal to the linear combination $a_1T_{10}+a_2T_{50}+a_3T_{90}+a_4EtOH+BuOH(a_5-a_6E200)$ below the maximum limit for Driveability Index (DI) for the specific class of gasoline.

15. The method of claim 1, further comprising adding one or more additives to the gasoline blend.

16. The method of claim 15, wherein the one or more additives are detergents, antioxidants, stability enhancers, demulsifiers, corrosion inhibitors, metal deactivators, or mixtures thereof.

17. The method of claim 1, wherein the gasoline is conventional gasoline, oxygenated gasoline, reformulated gasoline, biogasoline, Fischer-Tropsch gasoline, or mixtures thereof.

18. The method of claim 1, wherein the at least one biologically-sourced butanol isomer and gasoline are blended at a terminal or at a refinery.

19. The method of claim 9, further comprising adding one or more additives to the gasoline blend.

20. The method of claim 19, wherein the one or more additives are detergents, antioxidants, stability enhancers, demulsifiers, corrosion inhibitors, metal deactivators, or mixtures thereof.

21. The method of claim 9, wherein the gasoline is conventional gasoline, oxygenated gasoline, reformulated gasoline, biogasoline, Fischer-Tropsch gasoline, or mixtures thereof.

22. The method of claim 9, wherein the at least one biologically-sourced butanol isomer and gasoline are blended at a terminal or at a refinery.

\* \* \* \* \*